United States Patent [19]
Vogeler

[11] Patent Number: 5,570,700
[45] Date of Patent: Nov. 5, 1996

[54] ELLIPTICAL BIOPSY PUNCH

[76] Inventor: Douglas M. Vogeler, 3587 Little Cottonwood Ln., Sandy, Utah 84092

[21] Appl. No.: 317,124

[22] Filed: Oct. 3, 1994

[51] Int. Cl.$^6$ ............................................. A61B 10/00
[52] U.S. Cl. ........................ 128/754; 606/172; 606/184
[58] Field of Search ................................ 128/749, 751, 128/754; 606/167, 172, 184

[56] References Cited

U.S. PATENT DOCUMENTS

| | | |
|---|---|---|
| 2,521,161 | 9/1950 | Grover . |
| 3,512,519 | 5/1970 | Hall ............................................ 128/754 |
| 3,577,979 | 5/1971 | van der Gaast ........................... 128/754 |
| 3,990,451 | 11/1976 | Gibbs ...................................... 128/754 |
| 4,018,228 | 4/1977 | Goosen . |
| 4,542,742 | 9/1985 | Winkelman et al. . |
| 4,716,901 | 1/1988 | Jackson et al. . |
| 4,832,045 | 5/1989 | Goldberger ............................. 128/754 |
| 5,183,053 | 2/1993 | Yeh et al. ............................... 128/754 |

*Primary Examiner*—Max Hindenburg
*Attorney, Agent, or Firm*—Frost & Jacobs

[57] ABSTRACT

An elliptical skin biopsy punch includes a blade which creates an elliptical incision in the skin of a patient, in which the blade's profile is circular, thereby allowing the biopsy punch to be rocked back and forth during the surgical procedure. Integral depth guards are provided which prevent the blade from penetrating too deeply into the skin membrane, and which help to inform the physician when the incision has been completed. An aperture or window is provided so the physician can directly view the skin lesion while positioning the biopsy punch before the start of the incision. The upper portion of the biopsy punch has alignment marks to help in correctly positioning the biopsy punch around the skin lesion. Several different sizes of elliptical skin biopsy punch can be made so that the proper incision will be used for any particular skin lesion's size. Several different handle shapes are available for various sized lesions and various types of physician's hands. After the excision of the skin lesion, the result is a cosmetically ideal ellipse which can then be closed in a flat, straight suture line. A method for using the elliptical skin biopsy punch is also disclosed.

16 Claims, 9 Drawing Sheets

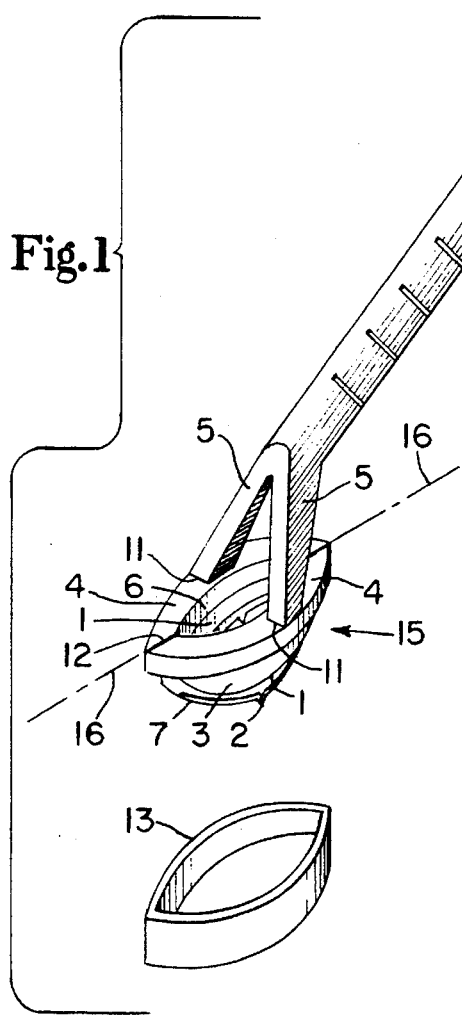
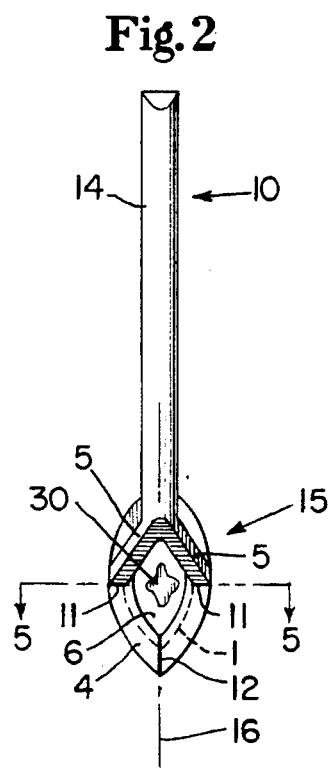
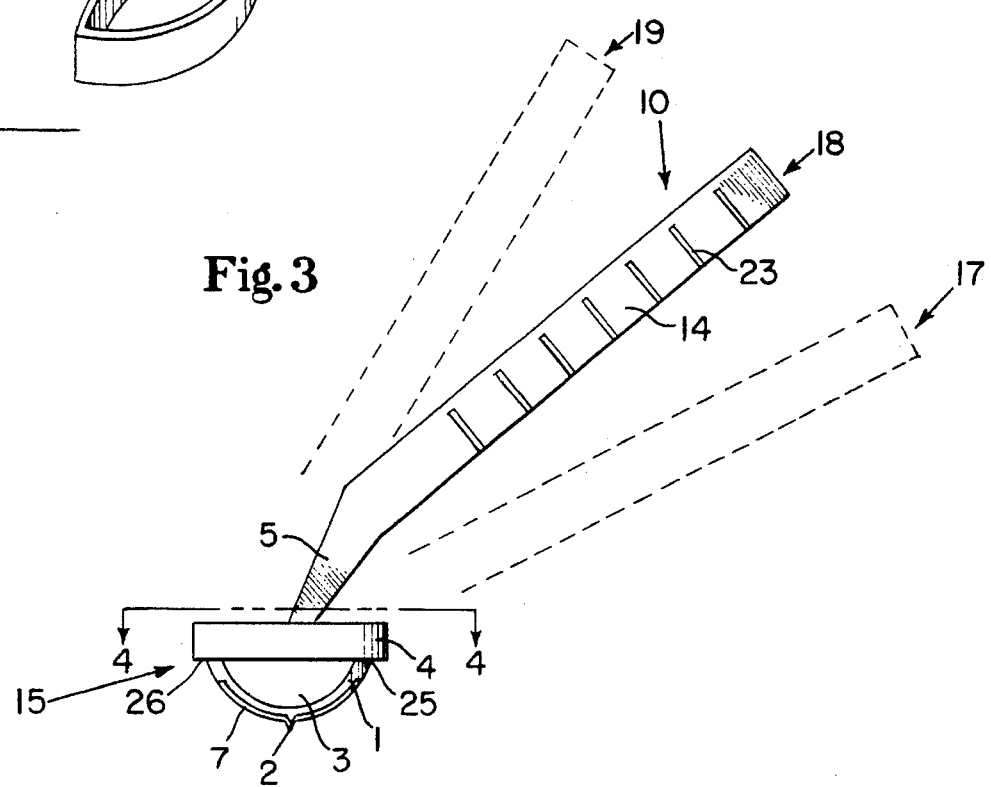

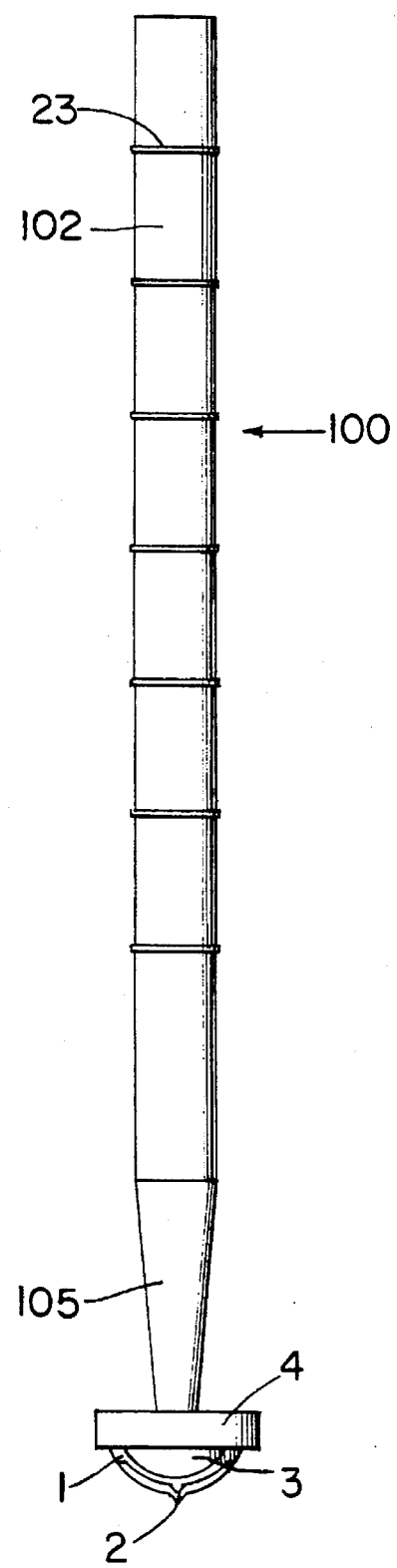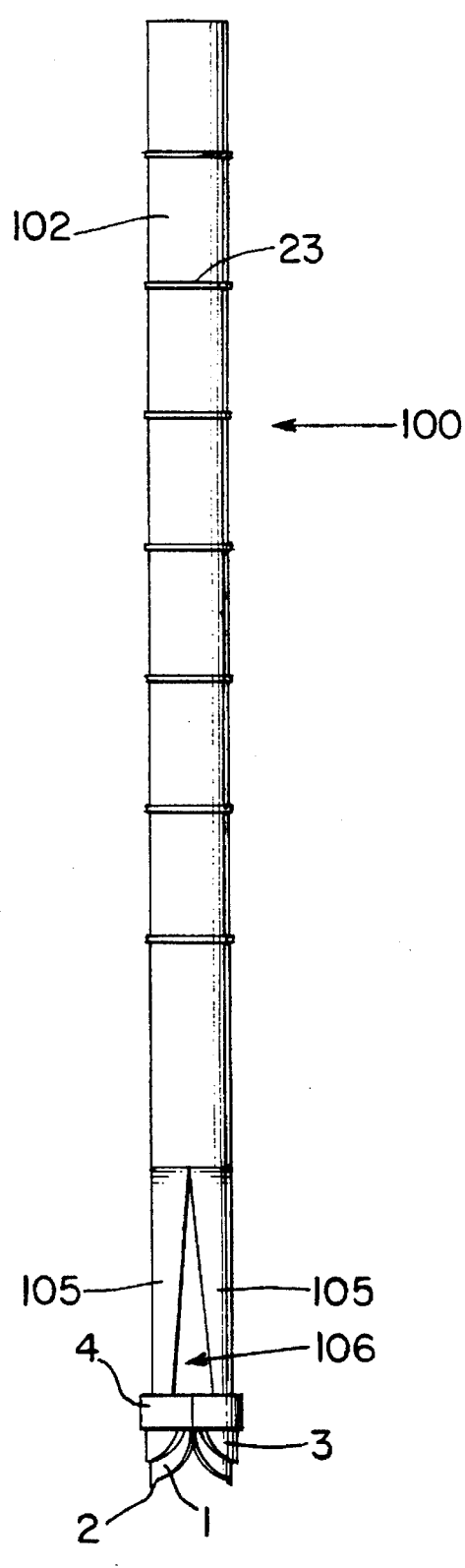

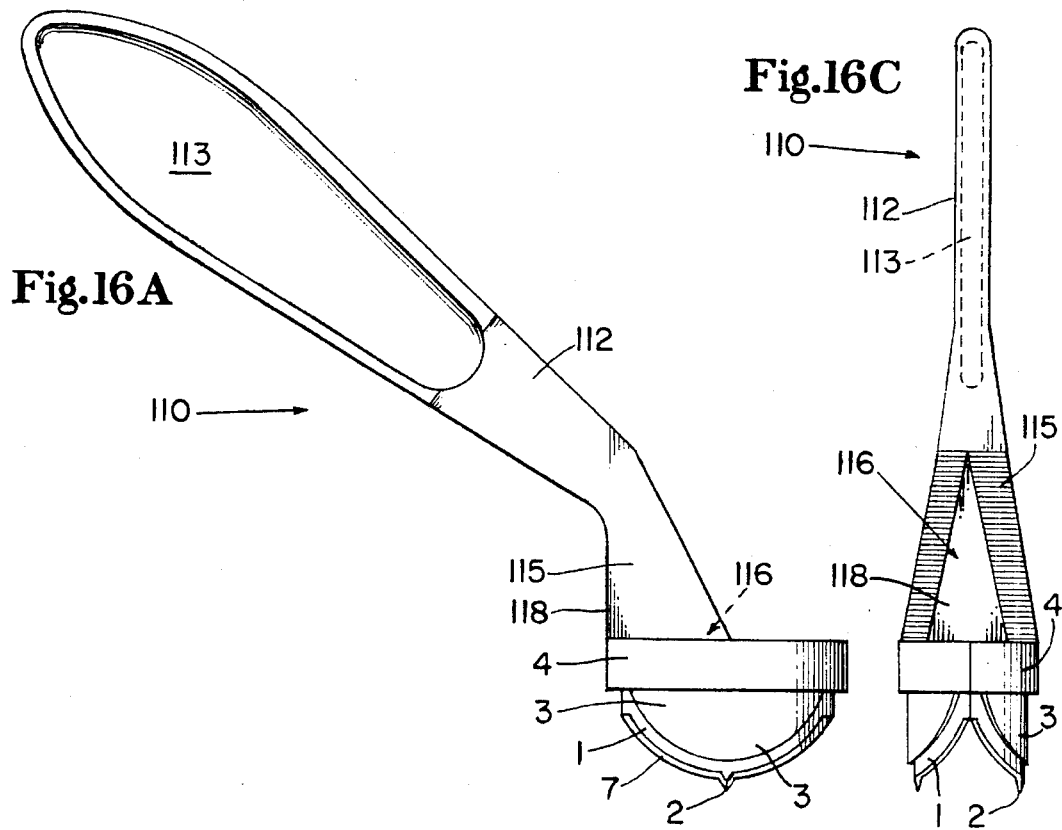
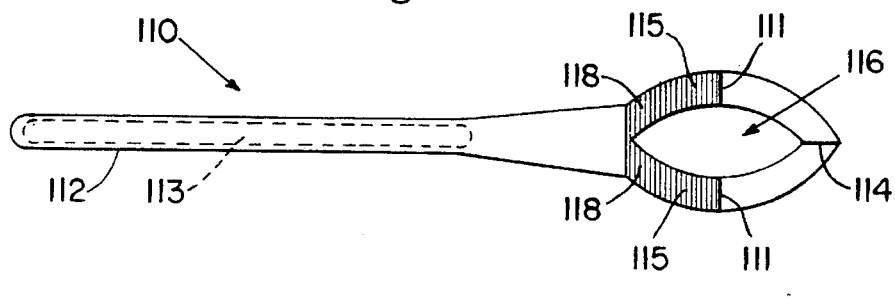

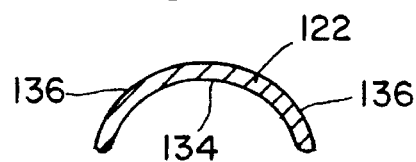
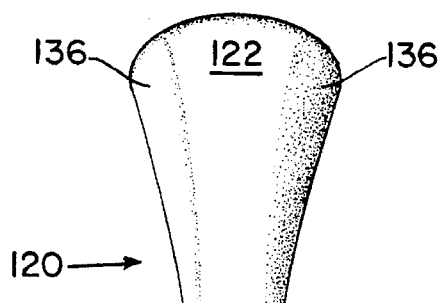
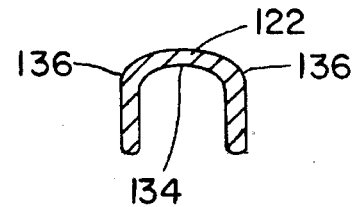
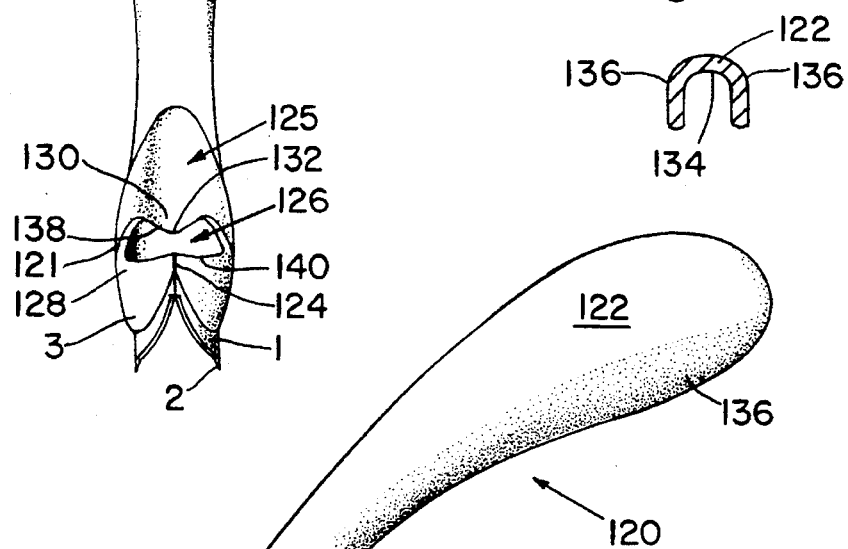
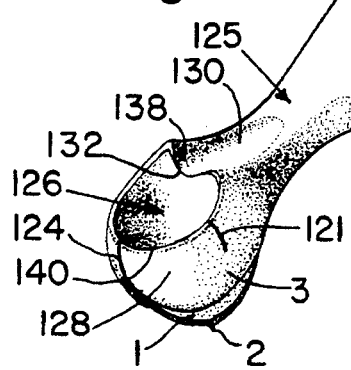

ELLIPTICAL BIOPSY PUNCH

TECHNICAL FIELD

The present invention relates generally to surgical equipment and is particularly directed to a skin biopsy punch of the type which is used to excise skin lesions. The invention is specifically disclosed as an elliptical skin biopsy punch that has a semicircular blade profile, anchoring lancet, direct lesion viewing aperture or window, and integral depth guard.

BACKGROUND OF THE INVENTION

The increased outdoor activities of many persons unfortunately causes an increased incidence of melanomas and skin cancers. Skin cancers are now the most common type of cancers in men and women in the United States, and are dramatically increasing each year. A primary care physician may excise several pre-cancerous or cancerous skin lesions per month.

A skin lesion smaller than 0.5 cm (0.20 inches) in diameter can be carefully removed by a physician using a scalpel or circular biopsy punch. The physician may then choose to either leave the wound open or to close it with a single suture. If a circular incision is used to remove a lesion that is greater than 0.5 cm in diameter, the subsequent suturing leaves a typical "smile-shaped" line with protruding ears, commonly called "Dog Ears".

To properly remove a lesion that is greater than 0.5 cm in diameter, a physician cuts an elliptical incision around the lesion, then sutures the two edges of the elliptical incision together. The result is a suture line which is straight and flat in appearance. This is the cosmetically preferred means for closing wounds from larger excised lesions. If the elliptical incision made by the physician, however, is too short and is proportioned more like a circle, the incision will also end up with "Dog Ears" when sutured. The ideal size ratio of length to width (major axis to minor axis) for the elliptical incision is 2.5 to 1.0 (2.5:1), however, other ratios up to 4.0 to 1.0 (4:1) could be used. This 2.5:1 ideal ratio holds true for all incisions that are greater than 0.5 cm (along the minor axis).

Some surgical devices presently available are capable of cutting a hole in a skin or other membrane surface. For example, U.S. Pat. No. 4,018,228 by Goosen discloses a surgical punch instrument that can create a hole in a hollow structure, such as the aorta or an eye. A small slit is cut in the aorta, for example, an outer blade is slid into the slit, then retracted against an inner blade, thereby cuffing a hole in the wall of the aorta. Another surgical appliance is disclosed in U.S. Pat. No. 4,716,901 by Jackson et al., which is a trocar that forms a hole in the skin so as to place appliances into a patient's body (e.g., drainage tubing). Two cutting edges are formed at opposite ends from a pair of hinged components, through which the trocar is inserted into a small skin opening when the tool is in its closed position. A rigid expander is then inserted near the hinges, causing the hinge components to separate, thereby expanding the slit in the skin. The appliance (i.e., the tubing) can then be inserted through the hollow expander.

Another surgical cutting instrument is disclosed in U.S. Pat. No. 2,521,161 by Grover, which acts as a meniscotome that cuts with a slicing action and allows removal of a meniscus. Another surgical instrument presently available is disclosed in U.S. Pat. No. 4,542,742 by Winkelman et al., and provides an elliptical cutting guide for skin lesion surgery. The Winkelman et al. disclosure describes the preferred ratio of the ellipse axes to be either 4 to 1 (4:1), or for larger wounds 3 to 1 (3:1). The elliptical guide is used as a template for the blade of a surgeon while excising a portion of skin.

None of the presently available surgical appliances is capable of creating an elliptically shaped, punched hole for use in removing skin lesions. Although the Winkelman et al. device can be used to assist in creating elliptically-shaped incisions, it has no means for actually creating the incision and requires the surgeon to use a scalpel or other surgical device to perform the actual cutting of the skin surface.

SUMMARY OF THE INVENTION

Accordingly, it is a primary object of the present invention to provide an easy method for excising larger skin lesions by cutting a cosmetically ideal ellipse which can then be closed in a flat, straight suture line.

It is another object of the present invention to provide a disposable, single-use surgical instrument which creates an elliptically-shaped biopsy incision, and operates by a punching action into the skin membrane.

It is a further object of the present invention to provide a disposable, single-use surgical instrument which exhibits a semi-circular blade profile when viewed from its side, so that the cutting angle of the surgical instrument with respect to the skin surface remains a near constant as the surgical instrument is rocked back and forth to perform the actual cutting operations into the skin membrane.

It is yet another object of the present invention to provide a disposable, single-use elliptical skin biopsy punch having a direct lesion viewing aperture or window, so that the physician can easily observe the placement of the biopsy punch around the lesion to be excised, and to observe the actual cutting operation while it is being performed by the physician.

It is still another object of the present invention to provide a disposable, single-use elliptical skin biopsy punch that includes an integral depth guard that prevents the physician from penetrating the skin too deeply during the cutting procedure. The integral depth guard can be partially removable, so that an increased depth can be achieved for certain areas of skin on a person's body.

A yet further object of the present invention is to provide a disposable, single-use elliptical skin biopsy punch having a V-shaped viewing aperture or window, that aids the physician in the placement of the biopsy punch around the lesion to be excised, and to observe the actual cutting operation while it is being performed by the physician.

Yet another object of the present invention is to provide a disposable, single-use elliptical skin biopsy punch having a finger placement pad near the base of the punch that allows the physician to readily apply pressure against the skin of the lesion to be excised.

Additional objects, advantages and other novel features of the invention will be set forth in part in the description that follows and in part will become apparent to those skilled in the art upon examination of the following or may be learned with the practice of the invention.

To achieve the foregoing and other objects, and in accordance with one aspect of the present invention, an improved disposable, single-use elliptical skin biopsy punch is provided having a semi-circular blade profile, anchoring lancets, a direct lesion viewing aperture or window, a handle which is curved, straight, or straight with an angular bend, and an integral depth guard. The curved or angled handle is connected to an elliptical pedestal by at least two supports, which supports thereby provide a separation allowing the physician's vision to be unobstructed through the direct lesion viewing aperture or window during the surgical procedure. The elliptical pedestal is available in various sizes, depending upon the size of the lesion to be excised. Attached to the bottom surfaces of the elliptical pedestal are a specially curved stainless steel blade and an integral depth guard. The sides of the blade may be angled outwardly at a 5° to 10° angle. The aperture or window offers the physician a direct view of the lesion for precise alignment of the biopsy punch. The elliptical skin biopsy punch can be supplied with any one of many various handle shapes for ease of use in excising lesions of different sizes. For very small skin lesions, the handle can be attached perpendicular to the elliptical pedestal. For medium sized skin lesions, the handle can be angled, either with or without a bulged lower surface; the bulged lower surface can further be optionally provided with notches to more readily "grip" the surgeon's fingers. For larger skin lesions, the handle can be more massive in size and curved for a more natural grip while attempting to apply a greater force to the patient's skin surface.

To perform the surgical procedure, the elliptical blade is placed against the skin, centering the lesion between the two anchoring lancets, then downward pressure is provided against the skin while simultaneously performing a rocking motion to the handle of the instrument. The integral depth guard prevents the blade of the biopsy punch from entering too deeply into the skin and the muscle structure below. A perfect elliptical incision can be made each time the procedure is performed by use of this surgical instrument. The slight outward angle of the blades is intended to square-off the skin as the blades are cutting, thereby improving the quality of the incision and resultant scar. If a deeper cut is required for a certain section of skin, a portion of the depth guard can be removed, thereby increasing the portion of exposed blade edge. This will increase the depth of penetration of the elliptical blade, so that a larger portion of skin membrane will be excised, and will allow for a greater utilization of a single biopsy punch.

Some of the alternate handle embodiments include a bulged handle that can additionally have finger grips, a curved and bulged handle, a shorter handle that is held by the thumb and index finger of the physician, a handle comprising two short handles that would each be held by the thumbs and index fingers of both hands of the physician, a straight handle at 90° for excising small lesions, and a curved handle having a finger placement pad for applying pressure directly at the blades of the biopsy punch. In addition, the viewing aperture or window can be a V-shape to assist in "aiming" the skin biopsy punch exactly as required to excise the lesion.

Still other objects of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

FIG. 1 is a perspective view of a disposable elliptical skin biopsy punch constructed in accordance with the principles of the present invention.

FIG. 2 is a plan view of the elliptical skin biopsy punch depicted in FIG. 1.

FIG. 3 is a left side elevational view of the elliptical skin biopsy punch depicted in FIG. 1.

FIG. 8 includes a bulged version of the angled handle of FIG. 7.

FIG. 9 includes a curved handle.

FIG. 15A is a side elevational view of a yet further alternate embodiment of the elliptical skin biopsy punch, having a straight handle for use in incising smaller lesions.

FIG. 15B is a front elevational view of the elliptical skin biopsy punch depicted in FIG. 15A.

FIG. 16A is a side elevational view of yet another alternate embodiment of the elliptical skin biopsy punch, having an angled handle with a closed rear end at the attachment point of the handle to the pedestal.

FIG. 16B is a top plan view of the elliptical skin biopsy punch depicted in FIG. 16A.

FIG. 16C is a front elevational view of the elliptical skin biopsy punch depicted in FIG. 16A.

FIG. 17 is perspective view of a disposable elliptical skin biopsy punch having a finger placement pad, constructed in accordance with the principles of the present invention.

FIG. 18C is a front elevational view of the elliptical skin biopsy punch depicted in FIG. 17.

FIG. 19A is a section view of the elliptical skin biopsy punch taken through the line 19A—19A shown in FIG. 18A.

FIG. 19B is a section view of the elliptical skin biopsy punch taken through the line 19B—19B shown in FIG. 18A.

FIG. 19C is a section view of the elliptical skin biopsy punch taken through the line 19C—19C shown in FIG. 18A.

DETAILED DESCRIPTION OF THE PREFERRED EMBODIMENT

Figure 4:
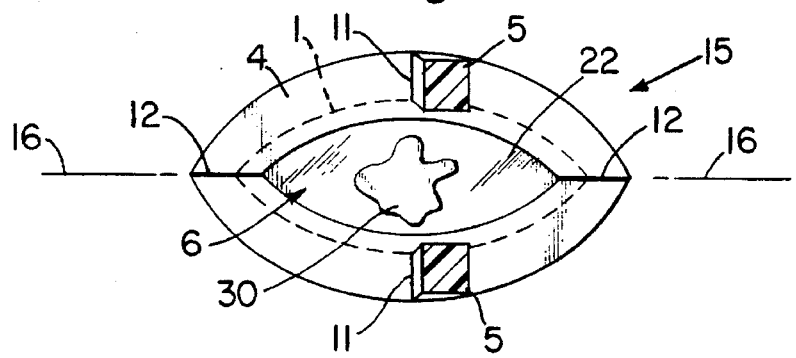
FIG. 4 is a section view of the elliptical skin biopsy punch taken through the line 4—4 shown in FIG. 3.

Reference will now be made in detail to the present preferred embodiment of the invention, an example of which is illustrated in the accompanying drawings, wherein like index numerals indicate the same elements throughout the views.

Referring now to the drawings, FIG. 1 shows a hand-held elliptical skin biopsy punch, generally designated by the index numeral 10, having an upper handle portion 14, and a lower elliptical portion 15. Handle 14 is joined to the lower portion 15 by a pair of supports 5, which are mounted on opposite sides of an elliptical pedestal 4. The shape of the elliptical pedestal provides an opening or aperture 6 to allow easy vision through the center portions of biopsy punch 10. Handle 14 preferably has a grip surface 23 which can comprise a series of score-like recesses, a series of embossed ribs, or a knurled-type surface along the length of the handle.

The longitudinal axis of biopsy punch 10, depicted as line 16, coincides with the major axis of the elliptical shape of elliptical pedestal 4. Longitudinal axis 16 additionally coincides with a "horizontal" alignment mark 12, which is one of the alignment marks used by the physician when performing the surgical procedure using biopsy punch 10. A similar "vertical" alignment mark 11, is disposed at a right angle to horizontal alignment mark 12, and coincides with the minor axis of the elliptical shape of elliptical pedestal 4.

Figure 5A:
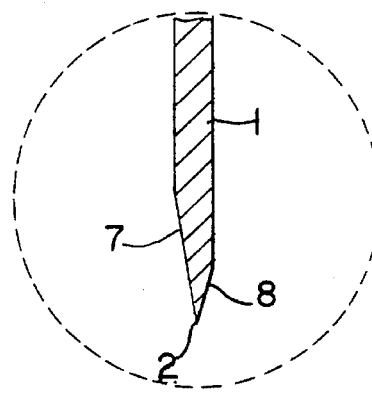
FIG. 5A is a fragmentary enlarged section view of the blade edge near the lancets.

An external depth guard 3 preferably is integrally attached to the bottom portions of elliptical pedestal 4. A cutting blade 1 is also integrally attached to the bottom portions of elliptical pedestal 4, and has a contour or profile which is similar to the contour of external depth guard 3. In the illustrated embodiment of FIGS. 1 and 3, the profile of blade 1 is circular, and the external depth guard 3 has a similar circular profile that is somewhat recessed toward the elliptical pedestal 4. The cutting edge of blade 1 is a modified chisel shape along the locations designated by index numeral 7, and is depicted in greater detail in FIGS. 5 and 5A. An anchoring lancet 2 is located approximately at the mid-point along the cutting edge 7 of blade 1.

Elliptical skin biopsy punch 10 would typically be packaged in a sterile wrapper (not shown) which could be easily opened and could be used to contain and dispose of biopsy punch 10 once it had been used to excise a skin lesion. A blade guard 13 would preferably be attached to the bottom portions of elliptical pedestal 4, thereby covering blade 1 so that a physician or other person could not be injured by the handling of biopsy punch 10. The curved blade 1 is preferably made of stainless steel, whereas the remaining portions of biopsy punch 10 are preferably made of a molded plastic material that is disposable and suitable for single-use. In addition, blade guard 13 is preferably also made of some type of molded plastic or other inexpensive material that also would be readily disposable.

As seen in FIG. 2, the combination of aperture 6 and the configuration of supports 5 allows a physician's vision of a skin lesion 30 to be unobstructed as the physician is performing the surgical procedure. The vertical alignment marks 11 and horizontal alignment marks 12 are used by the physician to center biopsy punch 10 over the skin lesion 30. One common method of using biopsy punch 10 is to hold it over a patient's skin in with handle 14 aligned parallel to the surgeon's eyes, in which the "vertical" alignment marks 11 appear to comprise a "Y-axis" and the horizontal alignment marks 12 appear to comprise an "X-axis" (as in FIG. 2), thereby appearing as "vertical" and "horizontal" directions upon a plane parallel to the patient's skin.

These same alignment marks 11 and 12, as well as aperture 6 are depicted in FIG. 4, in which the elliptical shape of blade 1 is apparent as it parallels the similar elliptical shape of aperture 6. FIG. 4 also depicts an optional window 22 which is used to cover the top portion of aperture 6. Optional window 22 is substantially transparent so that the physician's vision of skin lesion 30 remains unobstructed as the physician is performing the surgical procedure. Optional window 22 can be used in conjunction with any type or shape of aperture 6 without departing from the principles of the present invention.

Figure 6:
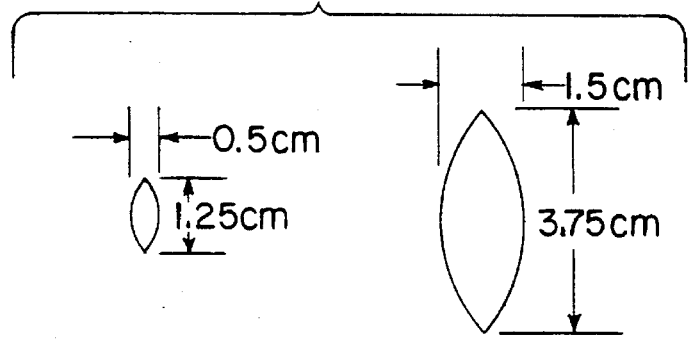
FIG. 6 illustrates some examples of elliptical hole sizes and shapes.

Elliptical skin biopsy punch 10 is preferably available in several different sizes of elliptical blade profiles, starting with a minor axis size of 0.5 cm. As described hereinabove, it is preferable to remove skin lesions that are greater than 0.5 cm in diameter using an elliptical incision rather than using a circular incision. Based upon that fact, elliptical skin biopsy punch 10 could be made available in incremental sizes, for example of 0.1 cm increments along its minor axis, so that the physician will easily be able to remove lesions of almost any size above 0.5 cm. Examples of the proper size and shape of the elliptical cutting profile are given in FIG. 6. As can be seen in FIG. 6, the ratio of the major axis to the minor axis of the elliptical cutting profile is 2.5 to 1 (2.5:1). A template (not shown) can be provided so that the physician can easily determine which size elliptical skin biopsy punch 10 should be used to excise any particular skin lesion. The physician would merely place the template over the skin lesion until the minor axis dimension was larger than the particular skin lesion. Once that dimension has been determined, the physician merely chooses the correct elliptical skin biopsy punch 10, having its minor axis at least as large as the skin lesion's diameter, and uses that biopsy punch for the surgical procedure.

When used in a surgical procedure, elliptical skin biopsy punch 10 is initially placed upon the patient's skin surface with only the anchoring lancets 2 touching the skin. The physician then provides pressure downward against the skin while simultaneously performing a rocking motion using handle 14. As seen in FIG. 3, the position of handle 14 will vary from a rear position designated by index numeral 17, through a neutral position 18, and to a forward position 19. As handle 14 is moved from neutral position 18 toward rear position 17, a rear cutting stop 25 will come into contact with the skin surface, thereby preventing any further rearward movement past rear position 17. Similarly, as handle 14 is moved from the neutral position 18 toward forward position 19, a forward cutting stop 26 comes into contact with the skin surface, thereby preventing any further forward movement past forward position 19.

Figure 5:
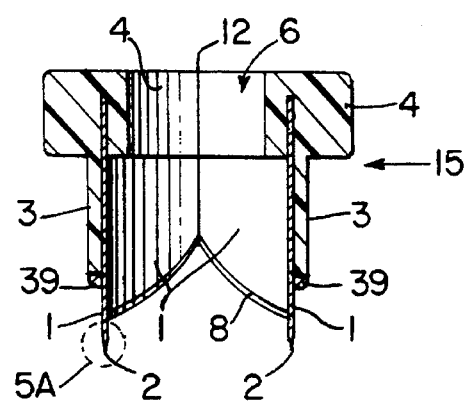
FIG. 5 is a section view of the elliptical skin biopsy punch taken through the line 5—5 shown in FIG. 2.

FIG. 5 depicts a more detailed view of a section of lower elliptical portion 15. In the illustrated embodiment of FIG. 5, elliptical pedestal 4 has two downward projections which form the external depth guards 3 and also which contain blade 1. As related hereinabove, except for the stainless steel blade 1, the remaining portion of elliptical skin biopsy punch 10 is preferably made of some type of molded plastic or thermo-plastic material. It is preferred that a combination of injection molding and metalplas insert molding techniques are used to mold the lower elliptical portion 15 around stainless steel blade 1, thereby providing a high quality, low cost disposable surgical instrument.

As viewed in FIG. 3, the bottom-most tips of blade 1 comprise the anchoring lancets 2. Lancets 2 are a preferred option that make it easier to place the initial position of biopsy punch 10 upon the skin surface, however, the lancets 2 are not required in the overall structure of blade 1. If lancets 2 are not used, the profile shape of external depth guard 3 would be changed to a minor extent so that a greater amount of cutting edge 7 is exposed near area 35 (see FIGS. 12 and 13, and a more detailed explanation of the shape of cutting edge 7, hereinbelow). The shape of the cutting edge of blade 1 is a modified chisel, as best viewed in FIG. 5A, and includes an outer cutting edge 7 and a shorter inner cutting edge 8. This modified chisel shape of blade 1 is accomplished by the double edge designated by the numerals 7 and 8 on FIGS. 1, 3, 5A, 12, and 13, and is continued all along its cutting edge. It will be understood that other shapes of the cutting edge may be used without departing from the principles of the present invention. Blade 1 may be everted by an angle of from between 5° to 10°, which assists in squaring off the skin as blade 1 is cutting.

As can be seen in FIG. 5, the external depth guard 3 limits the amount of penetration that blade 1 can make into the skin membrane. A portion of the depth guard can be removable so as to allow a deeper penetration of blade 1 into the skin membrane for applications where that is desirable or necessary. A removable portion 39 of external depth guard 3 is attached along the bottom-most surface of depth guard 3. Once the removable portion 39 has been detached from elliptical skin biopsy punch 10, then blade 1 can make a deeper penetration into the skin membrane.

Figure 12:
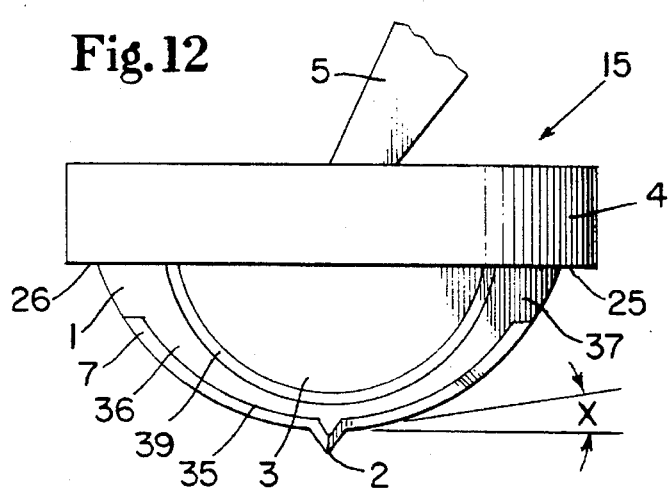
FIG. 12 is a fragmentary side elevational view of the elliptical skin biopsy punch of FIG. 1, having a removable depth guard attached, and depicting a constant cutting angle for efficient lesion removal.

Since the anchoring lancets 2 can assist in the removal of a skin lesion by slicing through the tissue on both the forward rocking and the rearward rocking strokes of blade 1, the exposed area 35 of blade 1 near anchoring lancet 2 need not be as great as the exposed area 36 of blade 1 near the forward cutting stop 26 (see FIG. 12). Similarly, the exposed area 35 of blade 1 near anchoring lancet 2 also need not be as great as the exposed area 37 of blade 1 at the rear cutting stop 25. During the rocking motion portions of the surgical procedure, the exposed areas 36 and 37 of blade 1 near the forward and rear cutting stops 26 and 25, respectively, only cut the skin half as frequently as the exposed area 35 near anchoring lancet 2.

FIG. 12 depicts the exposed areas 35, 36 and 37 with the removable portion 39 of external depth guard 3 in place.

Figure 13:
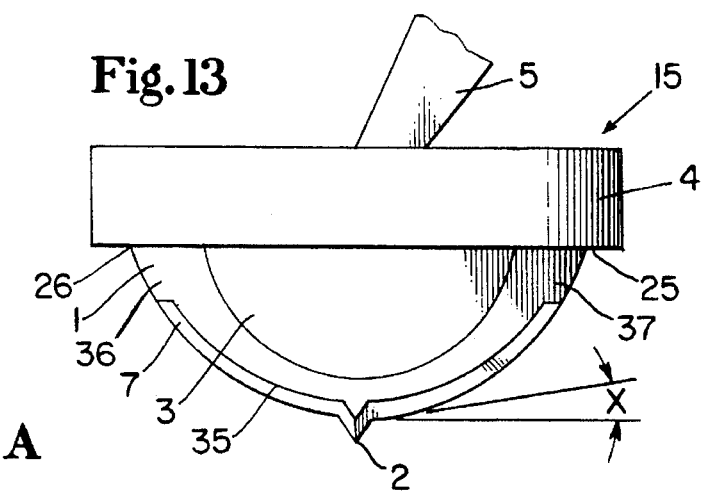
FIG. 13 is a fragmentary side elevational view of the elliptical skin biopsy punch of FIG. 1, in which the removable depth guard has been detached.

Once the removable portion 39 is detached from external depth guard 3, the same exposed areas 35, 36 and 37 are increased in dimension, as illustrated in FIG. 13.

Figure 14A:
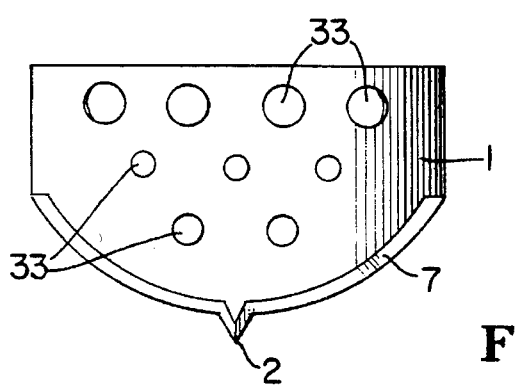
FIG. 14A is a side elevational view of the elliptically shaped blade used in the elliptical skin biopsy punch of FIG. 1.
Figure 14B:
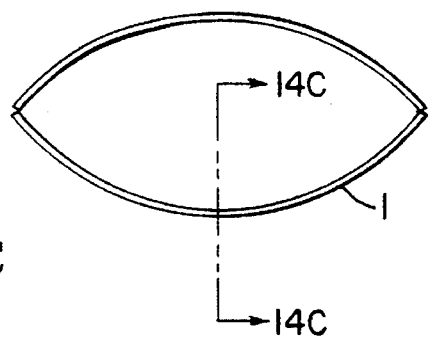
FIG. 14B is a top plan view of one-half of a blade used in the elliptical skin biopsy punch of FIG. 1.
Figure 14C:
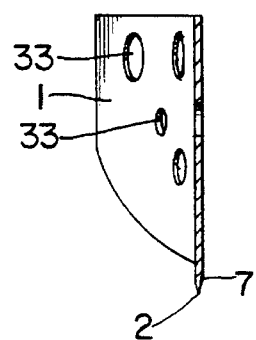
FIG. 14C is a section view, taken along the line C—C of FIG. 14B.

FIGS. 14A, 14B, and 14C depict a preferred construction of one-half of blade 1, having an elliptical shape, and additionally having a circular cutting profile. As can be seen in FIGS. 14A and 14B, blade 1 includes several through-holes 33, which reduce the amount of stainless steel material used in creating blade 1. In addition, through-holes 33 make it easier to manufacture the combination of the stainless steel blade 1 and the remaining portions of elliptical skin biopsy punch 10 (which are made of plastic), preferably via an injection molding process. As related hereinabove, current injection molding and metalplas insert molding techniques can be used to provide a high quality disposable instrument. Through-holes 33 allow the plastic to flow through and around such holes during the metalplas insert molding process, thereby insuring a strong mechanical connection between blade 1 and the remaining plastic portions of elliptical skin biopsy punch 10.

Figure 7:
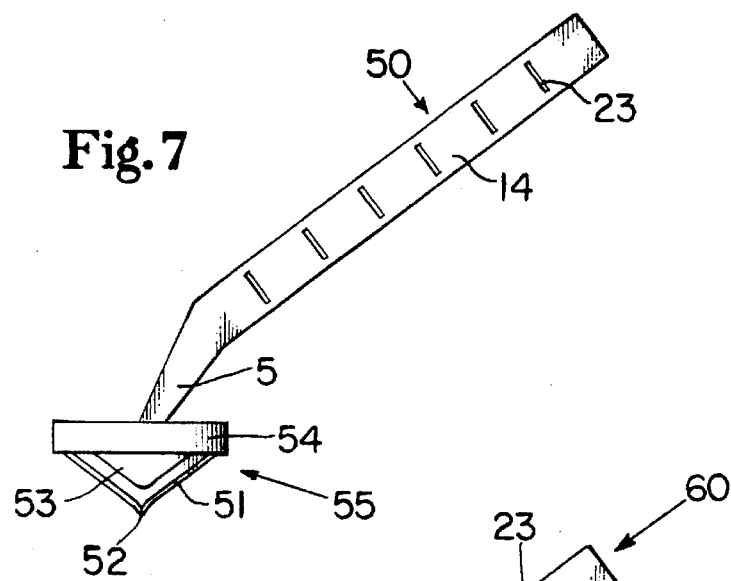
FIG. 7 is a side elevational view of an alternate embodiment of the elliptical skin biopsy punch, having a triangular blade profile with an angle of approximately 45°. The handle is angled with respect to the elliptical pedestal for more convenient handling by a surgeon.

An alternative embodiment 50 of an elliptical skin biopsy punch is depicted in FIG. 7. Biopsy punch 50 includes an angled handle 14, and a lower elliptical portion 55. Lower elliptical portion 55 comprises an elliptical pedestal 54, a blade 51 having a triangularly-shaped profile, anchoring lancets 52, and a triangularly-shaped external depth guard 53. As related above, for elliptical skin biopsy punch 10, handle 14 preferably has a grip surface 23 which can comprise a series of score-like recesses, a series of embossed ribs, or a knurled-type surface along the length of the handle. This alternative embodiment 50 may be less expensive to manufacture than elliptical skin biopsy punch 10 having a circular blade 1.

Alternate embodiment 50 would be used in a similar manner to excise a skin lesion, wherein the anchoring lancets 52 are first placed against the skin surface, then the entire elliptical skin biopsy punch 50 is pressed in a downward motion while rocking handle 14 back and forth to make the incision. One disadvantage, however, is that due to the triangular profile shape of blade 51, the cutting angle as blade 51 enters the skin will change as handle 14 is rocked back and forth. As handle 14 is rocked toward its rear position (similar to index numeral 17 on FIG. 3), the cutting angle between the edge of blade 51 and the surface of the skin becomes smaller, thereby requiring more force to actually make the incision. The same is true when handle 14 is brought into its forward position (similar to index numeral 19 on FIG. 3). The greater cutting force required would add to the discomfort of the patient.

Figure 8:
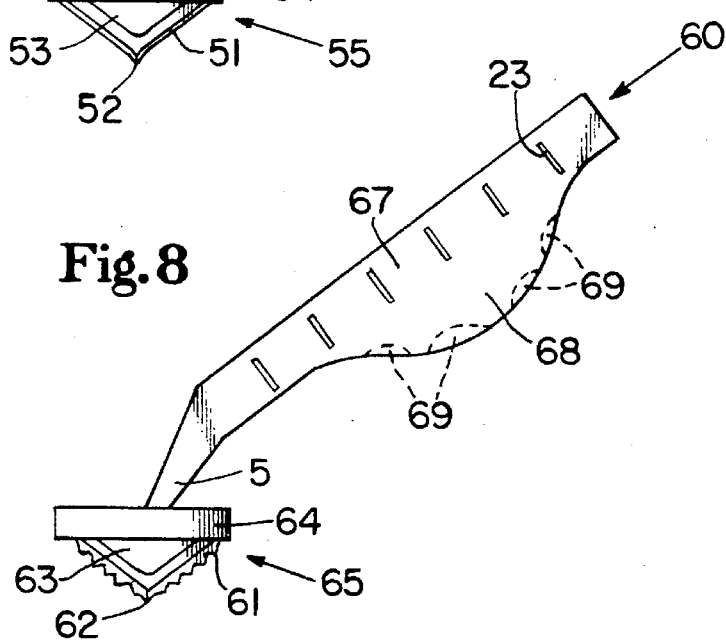
FIG. 8 is a side elevational view of another alternate embodiment of the elliptical skin biopsy punch, having a triangular blade profile with an angle of approximately 45°, and having serrated teeth.

A second alternate embodiment 60 of elliptical skin biopsy punch is depicted in FIG. 8, having many common features with the first alternate embodiment 50 of FIG. 7. Elliptical skin biopsy punch 60 also includes an angled handle 67 having an extra bulge 68 along its bottom surface, and a lower elliptical portion 65. Handle 67 preferably has a grip surface 23 which can comprise a series of score-like recesses, a series of embossed ribs, or a knurled-type surface along the length of the handle.

Because of its overall shape, bulged handle 67 may be easier for some surgeons to grip than the angled handle 14 depicted in FIG. 7. In particular, if optional notches 69 are included in the bulge portion 68 of bulged handle 67, the fingers of the surgeon will very easily grip the handle 67 without significant likelihood of slipping in position. It is preferred that the surgeon place his thumb along the top surface of bulged handle 67 while his four fingers are wrapped around the bulge portion 68 (and within notches 69, if they are available on a particular elliptical skin biopsy punch 60).

An elliptical skin biopsy punch having a bulged handle 67 is most useful when used with the medium punch sizes, such as those in the range of 0.5 cm to 3.0 cm (along their minor axis). It will be understood that bulged handle 67 can be used in lieu of angled handle 14 in all of the illustrated embodiments without departing from the principles of the present invention.

Lower elliptical portion 65 comprises an elliptical pedestal 64, a serrated blade 61 having a triangular profile, anchoring lancets 62, and a triangularly-shaped external depth guard 63. Although the blade 61 is triangular in shape, and therefore will require a greater operating force when the cutting angles change during the incision process, it is well known that a serrated blade will more easily cut through a membrane. Second alternate embodiment 60 will, therefore, be somewhat easier to use when making the incision as compared to first alternate embodiment 50, however, the serrated blade 61 will probably cost more to manufacture than the non-serrated blade 51. Bulged handle 67 is mounted to lower elliptical portion 65 by use of supports 5.

Figure 9:
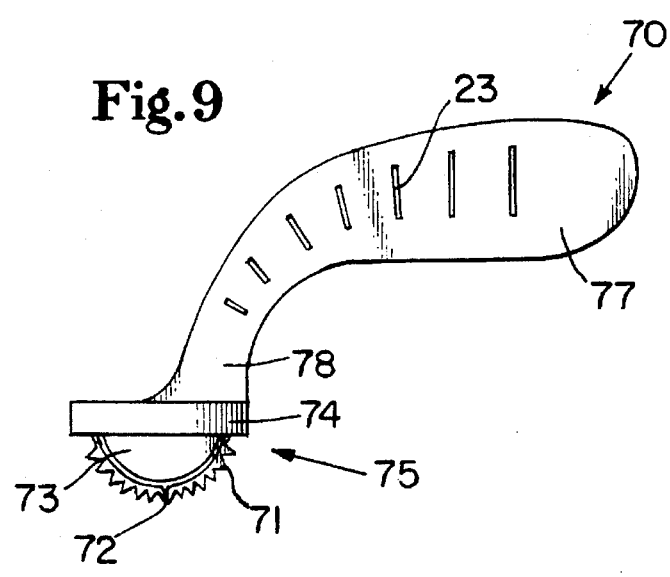
FIG. 9 is a side elevational view of still another alternate embodiment of the elliptical skin biopsy punch, having a circular blade profile, and additionally having serrated teeth.

A third alternate embodiment 70 of an elliptical skin biopsy punch is depicted in FIG. 9. Elliptical skin biopsy punch 70 includes a curved handle 77, as an alternative handle design, and a lower elliptical portion 75. Curved handle 77 may be easier for some surgeons to grip than the angled handle 14 depicted in the other figures. As in the case of other handles described herein, handle 77 preferably has a grip surface 23 which can comprise a series of score-like recesses, a series of embossed ribs, or a knurled-type surface along the length of the handle.

It will be understood that curved handle 77 can be used in lieu of angled handle 14 in all of the illustrated embodiments without departing from the principles of the present invention. An elliptical skin biopsy punch having a curved handle 77 is most useful when used with the larger punch sizes, such as those in the range greater than 3.0 cm along their minor axis.

Lower elliptical portion 75 comprises an elliptically-shaped pedestal 74, a serrated blade 71 having a circular profile, anchoring lancets 72, and a circularly-shaped external depth guard 73. Elliptical skin biopsy punch 70 has all of the advantages of ease of use of the elliptical skin biopsy punch 10 depicted in FIG. 3. In addition, as indicated above, it is well known that a serrated blade 71 will cut through membrane more easily than a non-serrated blade such as the blade 1 of elliptical skin biopsy punch 10. As best viewed in FIG. 12, the cutting angle "X" will be relatively constant when used with a circular blade 1 (or serrated blade 71), and will, therefore, require only a relatively constant cutting force as handle 14 is rocked back and forth during the surgical procedure. Although a circular blade 1 (or 71) will probably cost more to manufacture than a triangular blade 51 (or 61), the fact that it can be used with a relatively constant cutting force during the incision process is a distinct advantage, as it would be easier to use, and would cause less patient discomfort. Curved handle 77 is mounted to lower elliptical portion 75 by use of supports 78 (which are contoured somewhat differently than supports 5 used with angled handle 14 and bulged handle 67).

Figure 10:
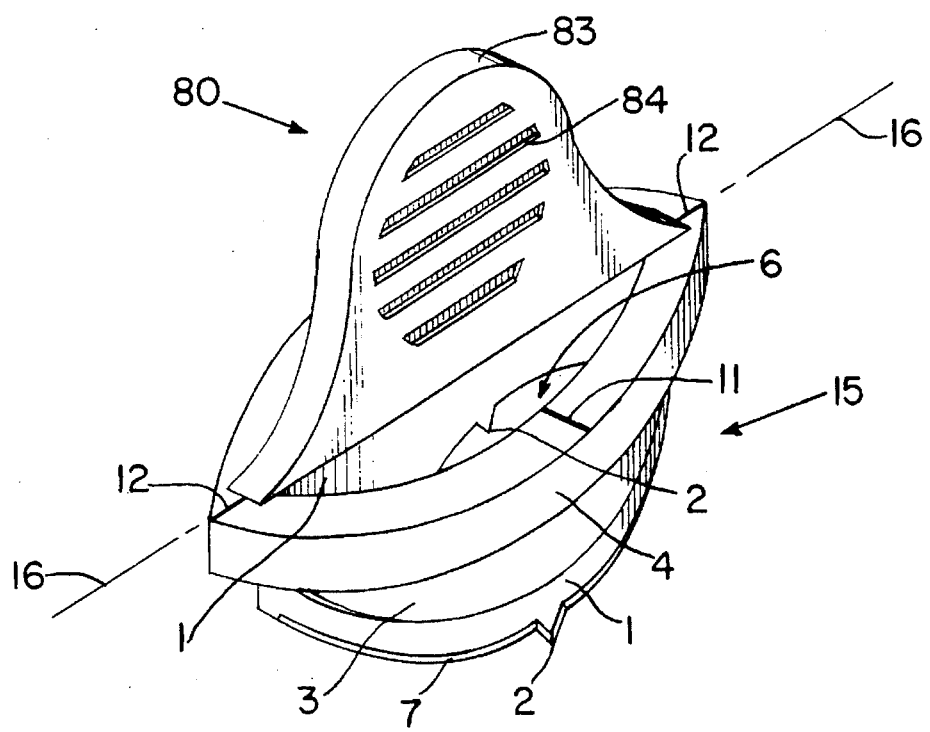
FIG. 10 is a perspective view of yet another alternate embodiment of the elliptical skin biopsy punch, having a short cutting handle that is held by the thumb and index finger of the physician while performing the surgical procedure.

A fourth alternate embodiment 80 of an elliptical skin biopsy punch is depicted in FIG. 10. Elliptical skin biopsy punch 80 does not have a long, extended handle, such as handle 14 in FIG. 3, but instead has a circular handle 83 which is gripped by the physician's thumb and index finger of one hand. The molded grip portion 84 of handle 83 is designed to facilitate the physician's handling of biopsy punch 80. Circular handle 83 is oriented in a plane that is substantially perpendicular to the upper surface of elliptical pedestal 4.

Biopsy punch 80 includes a lower elliptical portion 15 which includes an elliptical pedestal 4, external depth guard 3, cutting blade 1, and anchoring lancets 2. In addition, the top surfaces of elliptical pedestal 4 include vertical alignment marks 11 and horizontal alignment marks 12. The physician would take his free hand to align elliptical skin biopsy punch 80 using the vertical and horizontal alignment marks 11 and 12, while locating the skin lesion through aperture 6, and then proceed with the incision process.

Elliptical skin biopsy punch 80 is used in a similar manner to the embodiments described hereinabove, in which the punch is lowered to the stretched skin portion while placing the anchoring lancets 2 along opposite sides at an equal distance from the periphery of the skin lesion. While the physician is holding handle 33, elliptical skin biopsy punch 80 is pushed into the skin. A rocking motion is then applied to elliptical skin biopsy punch 80 along its is longitudinal axis 16, until the external depth guard 3 touches the skin. At that point, the surgical procedure has been accomplished and the skin lesion has been incised, and now can be excised.

Figure 11:
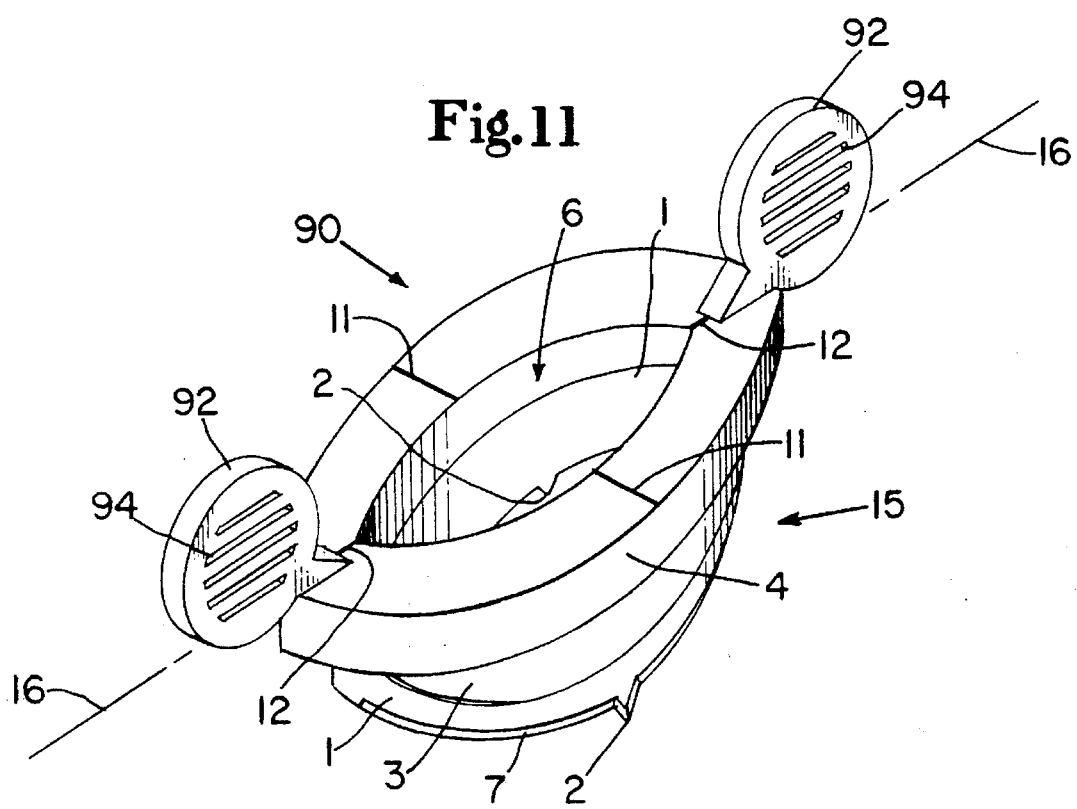
FIG. 11 is a perspective view of a further alternate embodiment of the elliptical skin biopsy punch, having two short cutting handles which would be held by both thumbs and index fingers of each hand of the physician while performing the surgical procedure.

A fifth alternate embodiment 90 of an elliptical skin biopsy punch is depicted in FIG. 11. Elliptical skin biopsy punch 90 includes two handles 92, each of which have molded grip portions 94. Handles 92 are attached to the distal ends of the major axis of an elliptically-shaped pedestal 4, which is included in the lower elliptical portion 15. The remainder of lower elliptical portion 15 is identical to the lower elliptical portion 15 depicted in FIG. 10. Circular handles 92 are oriented in a plane that is substantially perpendicular to the upper surface of elliptical pedestal 4.

To use elliptical skin biopsy punch 90, the physician applies tension to the skin area to be excised with the fingers of one hand, while simultaneously aligning biopsy punch 90 over the skin lesion, using the vertical and horizontal alignment marks 11 and 12. This is accomplished while viewing the skin lesion directly through aperture 6. The physician then lowers biopsy punch 90 to the stretched skin while placing the anchoring lancets 2 along opposite sides at an equal distance from the periphery of the skin lesion. The physician now places his hands on both handles 92, while pressing biopsy punch 90 in a downward direction and while simultaneously rocking biopsy punch 90 back and forth along its longitudinal axis 16. The rocking motion is continued until the external depth guard 3 touches the skin. At that point, the surgical procedure has been accomplished and the skin lesion has been incised, and now can be excised.

An elliptical skin biopsy punch having circular handles, such as handle 83 of biopsy skin punch 80 and handles 92 of biopsy skin punch 90, is most useful when used with the smaller punch sizes, such as those in the range in the range of 0.5 cm to 1.0 cm along their minor axis. It will be understood that an elliptical biopsy skin punch may be equipped with one of a single circular handle (such as handle 83), a pair of circular handles (such as handles 92), or a straight handle to be used on smaller sized lesions (such as handle 102—See FIG. 15A), in each of the illustrated embodiments without departing from the principles of the present invention. It will further be understood that variations in handle size and shape can be made to all versions of elliptical biopsy skin punch without departing from the principles of the present invention.

In comparing alternate embodiment 80 to alternate embodiment 90, it will be seen that the aperture 6 is more open in the biopsy punch embodiment 90 depicted in FIG. 11. However, elliptical skin biopsy punch 80 has sufficient clearance through its aperture 6 for the physician to see the skin lesion while aligning biopsy punch 80 over the skin lesion.

A sixth alternate embodiment 100 of an elliptical skin biopsy punch is depicted in FIGS. 15A and 15B. Elliptical skin biopsy punch 100 includes a straight handle 102, and is preferably used to incise lesions of smaller sizes. Handle 102 preferably has a grip surface 23, as described hereinabove. Handle 102 is attached, via supports 105, to an elliptical pedestal 4 of a type as described hereinabove.

FIGS. 15A and 15B show the side and front views, respectively, of the blade 1, anchoring lancets 2 and the external depth guard 3. In addition, FIG. 15B depicts an aperture 106 through which the physician can view the lesion to be excised while positioning elliptical biopsy punch 100 above the patient's skin surface. This alternate embodiment biopsy punch 100 is used in the same manner as the other biopsy punches previously described hereinabove.

FIGS. 16A, 16B, and 16C depict a seventh alternate embodiment 110 of an elliptical skin biopsy punch. As in the previously described embodiment 100, an elliptical pedestal 4 is depicted along with a blade 1, anchoring lancets 2, and an external depth guard 3. In the side view presented in FIG. 16A, an angled handle 112 is shown having a recessed grip portion 113. Recessed grip portion 113 can also be viewed in FIGS. 16B and 16C as bounded by the dashed lines.

Handle 112 is attached to elliptical pedestal 4 via a pair of supports 115, in which supports 115 are effectively joined together by a closed rear end portion 118 (as viewed in FIGS. 16A and 16C). Closed rear end portion 118 along with supports 115 do not, however, obstruct the view of the physician through the aperture 116, and elliptical biopsy skin punch 110 can be easily aligned to the patient's skin lesion by use of vertical alignment marks 111 and horizontal alignment mark 114. This can be easily seen in FIG. 16B. This seventh alternate embodiment biopsy punch 110 is used to incise skin lesions in the same manner as that of the other embodiments of the elliptical skin biopsy punch described hereinabove.

An eighth alternate embodiment depicted by the index numeral 120 of an elliptical skin biopsy punch is depicted in FIGS. 17, 18A–18D, and 19A–19C. As in the previously described embodiments, a blade 1, anchoring lancets 2, and external depth guard 3 are provided and are mounted into an integral elliptical pedestal designated by the index numeral 128. The perspective view of FIG. 17 shows that the curved handle 122, a "support" 125, and the elliptical pedestal 128, are all of a "one-piece" integral construction, and are preferably formed at one time in a plastic mold. It will be understood that different blade sizes than that illustrated in the drawings can be used with the same handle 122, support 125 and pedestal 128 without departing from the principles of the present invention. It is preferred that the blade, regardless of its size, be molded along with the other plastic parts of elliptical skin biopsy punch 120 to form the "one-piece" integral construction.

The integral support 125 includes a finger positioning pad, which has a surface that is depicted by the index numeral 130 for making contact with the physician's index finger during the act of making the incision. This contact surface 130 is placed such that the physician's index finger can directly apply pressure in a downward direction against the lower portions of biopsy punch 120 essentially directly against the portion of the skin having the lesion. In the construction illustrated for this embodiment 120, the physician's view through an aperture 126 is not blocked by either the finger pad contact surface 130 or by the physician's index finger when placed against that contact surface.

Skin biopsy punch 120 can be provided with alignment marks, such as a vertical alignment mark 121 and horizontal alignment mark 124. These marks can be used, as described hereinabove, to help guide the physician in centering the skin biopsy punch 120 over the lesion to be excised. As a further aid in guiding the placement of skin biopsy punch 120, the rear edge 138 of aperture 126 will preferably have a V-shaped notch or groove, which essentially acts as a "gun site" to help guide the "aim" of the physician who is about to press skin biopsy punch 120 against a patient's skin surface.

As can be best seen in FIG. 18C, the curved handle 122 has rounded sides designated by the index numeral 136. The same rounded sides are depicted in greater detail in the section views of FIGS. 19A, 19B, and 19C. In addition, the lower surface of curved handle 122 is preferable recessed, as depicted by the index numeral 134, and best seen in FIGS. 18D, 19A, 19B, and 19C. By shaping the handle in the manner illustrated, skin biopsy punch 120 will remain relatively light-weight, and will use less material than if the handle were much thicker.

Figure 18A:
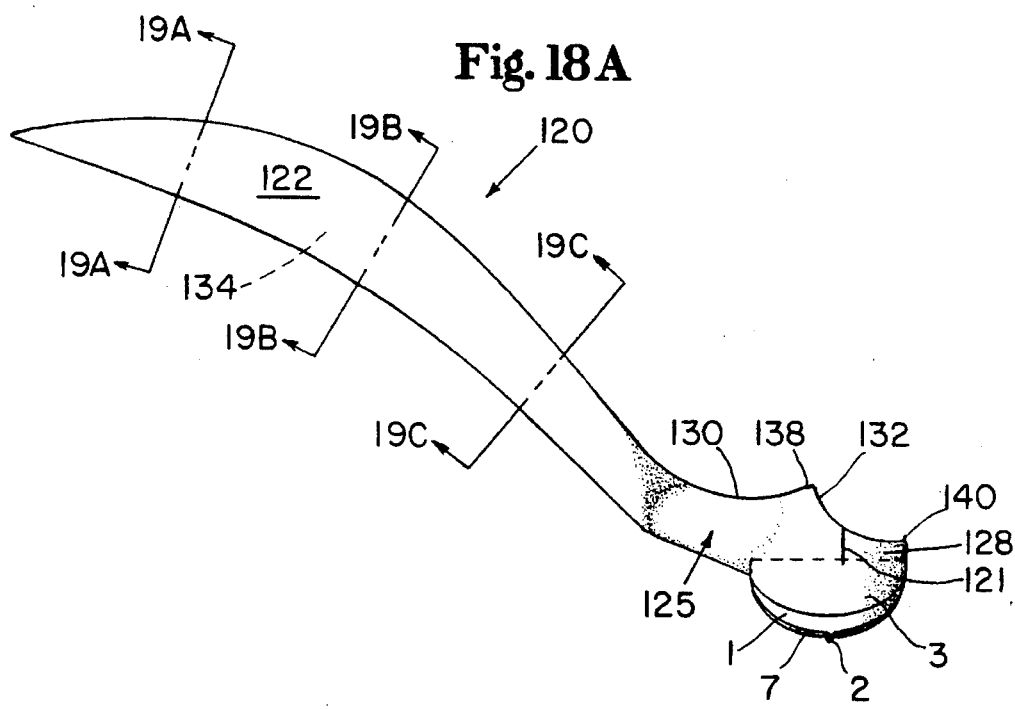
FIG. 18A is a right side elevational view of the elliptical skin biopsy punch depicted in FIG. 17.
Figure 18B:
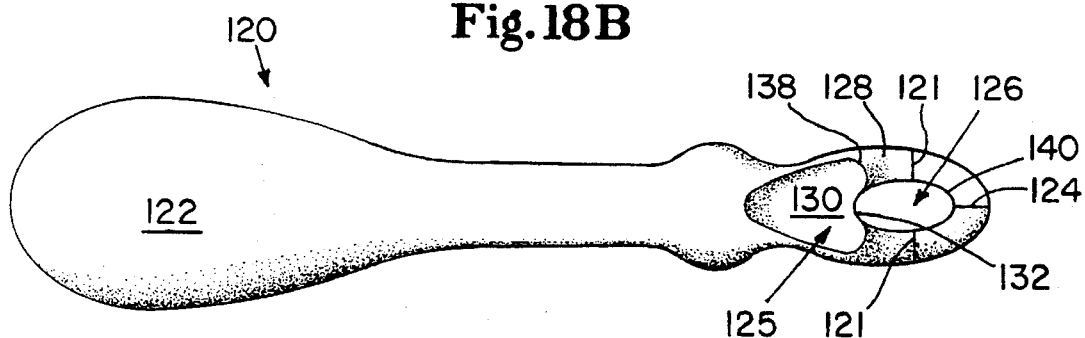
FIG. 18B is a top plan view of the elliptical skin biopsy punch depicted in FIG. 17.
Figure 18D:
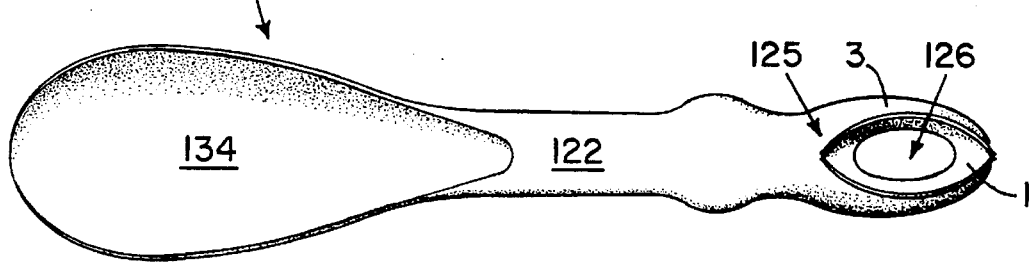
FIG. 18D is a bottom plan view of the elliptical skin biopsy punch depicted in FIG. 17.

The aperture 126 is preferably shaped with relatively smooth edges around its upper surfaces, while forming an overall elliptical shape as seen from above (as best viewed in FIG. 18B). To form the "gun site" or V-shaped notch or groove 132, the rear edge 138 is preferably constructed at a "higher" elevation as compared to the front (or "lower") edge of aperture 126, designated by the index numeral 140. This is best viewed in the front view of skin biopsy punch 120, depicted in FIG. 18C. Aperture 126 could, of course, optionally be provided with a transparent window (not shown) in a similar manner to the window 22 depicted in FIG. 4.

The arrangement of the integral components of skin biopsy punch 120 allows for ease of use and handling the punch by the physician's fingers, while also helping to guide the physician's view of the skin lesion about to be excised. This eighth alternate embodiment biopsy punch 120 is preferably used to incise skin lesions in the same manner as the use of the other embodiments described here and above.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

I claim:

1. A skin biopsy punch, comprising:
    (a) a first portion, including:
        (i) a handle for engagement by a user's hand, said handle having a first, free end and a second end;
        (ii) a support member fixedly attached to said second end of the handle;

(b) a second portion, including:
  (i) a pedestal member having an aperture through which the user may view an area of skin to be incised as said skin biopsy punch approaches said area, said pedestal member being fixedly attached to said support member in a manner such that said support member does not totally obscure the user's vision through said aperture;
  (ii) a blade having a cutting surface and being located on the opposite side of said pedestal from said first portion, said blade being configured to incise an area of skin; and
  (iii) a depth guard extending from said pedestal and along said blade, said depth guard exposing a predetermined portion of said blade for use in cutting skin, said depth guard exposing a different amount of said blade at varying distances along said cutting surface of the blade, said blade being fixedly attached to said depth guard.

2. The skin biopsy punch as recited in claim 1, further comprising at least one anchoring lancet located on said blade's cutting surface.

3. The skin biopsy punch as recited in claim 1, further comprising at least one alignment mark on said pedestal member, said at least one alignment mark so located as to assist the user in the correct placement of said skin biopsy punch during its use.

4. The skin biopsy punch as recited in claim 1, wherein the shape of said pedestal is substantially elliptical.

5. The skin biopsy punch as recited in claim 1, wherein the shape of said blade is substantially elliptical.

6. The skin biopsy punch as recited in claim 1, wherein said handle and said support member define a curve.

7. The skin biopsy punch as recited in claim 1, wherein said handle is substantially curved between its first and second ends.

8. The skin biopsy punch as recited in claim 1, wherein said support member forms a closed end at its point of attachment to the handle at said second end of the handle.

9. The skin biopsy punch as recited in claim 1, wherein said first and second portions are made primarily of curved surfaces which together create a smooth transition of fairing curves, such that said support member and said pedestal are both integral within the overall shape of said curved surfaces.

10. The skin biopsy punch as recited in claim 9, wherein said integral support member comprises a finger pad along its upper surface.

11. The skin biopsy punch as recited in claim 9, wherein said integral pedestal comprises a substantially elliptical shape.

12. The skin biopsy punch as recited in claim 9, wherein said integral pedestal includes an aperture that comprises an opening with an inner edge within said pedestal, said aperture inner edge being at a greater elevation, during use of said skin biopsy punch, at its rearmost portion proximal to said first portion, than at its forward-most portion distal from said first portion.

13. The skin biopsy punch as recited in claim 12, wherein said integral pedestal forms a V-shaped notch at said rearmost portion of said aperture.

14. A method of forming an excising incision, comprising the steps of:
  (a) aligning a skin biopsy punch while viewing a skin lesion to be excised through an aperture in said skin biopsy punch, said skin biopsy punch including a handle for engagement by a user's hand, a pedestal member containing said aperture, and a support member therebetween, said skin biopsy punch further including a blade configured to make a lesion-surrounding incision, wherein said blade is located on the opposite said of said pedestal from said handle, said blade being fixedly attached to a depth guard extending from said pedestal along said blade, said depth guard exposing a predetermined portion of said blade for use in cutting skin, said depth guard exposing a different amount of said blade at varying distances along said cutting surface of the blade; and
  (b) placing said skin biopsy punch onto the skin surface, and pressing down and rocking said biopsy punch alternatively back and forth to provide an elliptically-shaped incision about said skin lesion, said blade being further configured to have a profile that facilitates said rocking back and forth motion.

15. The method of claim 14, wherein the step of including a blade configured to make a lesion-surrounding incision includes providing a blade which creates an elliptically-shaped incision.

16. The method of claim 14, further providing the step of pressing at least one lancet into the skin as said skin biopsy punch is placed onto the skin surface.

* * * * *